(12) United States Patent
Hodorek

(10) Patent No.: US 6,797,006 B2
(45) Date of Patent: Sep. 28, 2004

(54) POROUS UNICONDYLAR KNEE

(75) Inventor: Robert Hodorek, Warsaw, IN (US)

(73) Assignee: Zimmer Technology, Inc., Chicago, IL (US)

( * ) Notice: Subject to any disclaimer, the term of this patent is extended or adjusted under 35 U.S.C. 154(b) by 0 days.

(21) Appl. No.: 10/174,352

(22) Filed: Jun. 18, 2002

(65) Prior Publication Data
US 2003/0233149 A1 Dec. 18, 2003

(51) Int. Cl.[7] ................................. A61F 2/38
(52) U.S. Cl. ..................... 623/20.36; 623/20.17
(58) Field of Search ................ 623/20.14, 20.15, 623/20.17, 20.3, 20.35, 20.36

(56) References Cited

U.S. PATENT DOCUMENTS

| | | | |
|---|---|---|---|
| 5,226,915 A | * | 7/1993 | Bertin ................. 623/20.15 |
| 5,336,266 A | * | 8/1994 | Caspari et al. ......... 623/20.35 |
| 5,358,529 A | * | 10/1994 | Davidson ............. 623/20.19 |
| 5,571,194 A | | 11/1996 | Gabriel |
| 5,645,602 A | | 7/1997 | Bjorn et al. |
| 5,879,391 A | * | 3/1999 | Slamin ................. 623/20.15 |
| 6,136,029 A | | 10/2000 | Johnson et al. |
| 6,171,340 B1 | | 1/2001 | McDowell |
| 6,245,110 B1 | * | 6/2001 | Grundei et al. ......... 623/20.31 |

FOREIGN PATENT DOCUMENTS

| | | |
|---|---|---|
| FR | 2738739 | 12/1997 |
| FR | 2758715 | 4/1999 |

* cited by examiner

*Primary Examiner*—Corrine McDermott
*Assistant Examiner*—Thomas J Sweet
(74) *Attorney, Agent, or Firm*—Jonathan D. Feuchtwang; Zimmer Technology Inc.

(57) ABSTRACT

A unicondylar femoral component for use in a partial knee arthroplasty. A femoral component of the present invention comprises a post and a flange having a pre-determined angle there between whereby a clamping force is placed on a patient's distal femur to hold the implant in place. The implant further comprises a porous layer on its bone contacting surface. In an alternative embodiment the femoral component is attached to the distal femur at least two threaded fasteners.

6 Claims, 2 Drawing Sheets

POROUS UNICONDYLAR KNEE

BACKGROUND OF THE INVENTION

1. Field of the Invention

The present invention relates to unicondylar or partial knee arthroplasty, specifically the invention relates to a femoral component used during such an operation.

2. Description of the Related Art

Total knee arthroplasty ("TKA") has long been a successful treatment for patients who have knee joints that have been damaged by disease or trauma. During a TKA a patient's damaged knee is replaced with an endoprosthetic implant generally comprising a femoral component, a bearing component, and a tibial component wherein the femoral component is attached to the distal femur of the patient. This fixation occurs in part via a clamping force against the distal femur generated between the posterior and anterior flanges of the femoral component. Femoral components used during a TKA may further comprise a porous surface that promotes growth of bone into the implant. Such boney ingrowth provides better fixation of the implant and for a more accurate simulation of a natural knee.

Sometimes, however, a patient's knee is only partially damaged, thus it is sometimes only necessary to fix one compartment, or condyle, of the damaged knee. It is desirable in such circumstances to form a partial knee arthroplasty ("PKA") which normally requires less surgical cutting and therefore less trauma to the patient. Unfortunately, unicondylar femoral components do not have posterior flanges with which the anterior flange can generate a clamping force against a distal femur. It is desirable, therefore, to provide a unicondylar femoral component for a PKA that may be attached to a distal femur despite lacking a posterior flange. It is further desirable to provide a unicondylar femoral component for a PKA that comprises a porous surface useful in promoting boney ingrowth.

SUMMARY OF THE INVENTION

A unicondylar femoral component for use in a PKA according to the present invention comprises, in one embodiment thereof, an articulating surface, a bone contacting surface, a posterior post, a porous layer, and an anterior flange. The post and flange are disposed such that a clamping force is generated there between against a prepared distal femur thereby holding the implant in place.

In a second embodiment, the present invention comprises an articulating surface, a bone contacting surface, a posterior post, an anterior post, and a porous layer wherein the clamping force against the distal femur is generated between the posterior and anterior posts.

In a third embodiment, the unicondylar femoral component of the present invention comprises an articular surface, a bone contacting surface, a porous layer disposed on the bone contacting surface and at least two threaded fasteners that are threaded through the femoral component and into the distal femur.

It is an advantage of the present invention that it allows a unicondylar femoral component to be fixedly attached to a distal femur.

Another advantage of the present invention is that it accommodates a porous layer disposed on the bone contacting surface of the femoral component.

Another advantage of the present invention is that it allows for the use of a trabecular metal porous layer.

Other advantages and features of the present invention will be apparent to those skilled in the art upon a review of the appended claims and drawings.

BRIEF DESCRIPTION OF THE DRAWINGS

The above mentioned and other features and advantages of this invention and the manner of obtaining them will become more apparent, and the invention itself will be better understood by reference to the following description of an embodiment of the invention taken in conjunction with the accompanying drawings, wherein.

Figure 1:
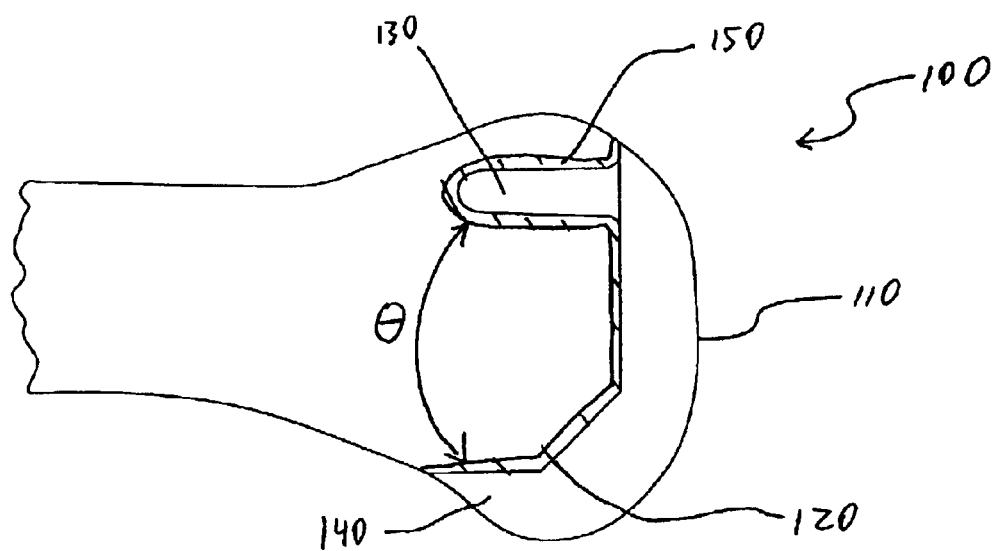
FIG. 1 is a side elevational view of a first embodiment of the present invention.

Corresponding reference characters indicate corresponding parts throughout the several views. Although the drawings represent an exemplary embodiment of the present invention the drawings are not necessarily to scale and certain features may be exaggerated to better illustrate and explain the invention. The illustrations set out herein merely illustrate exemplary embodiments of the present invention.

DETAILED DESCRIPTION OF THE INVENTION

As used herein, the following locational definitions apply, anterior or posterior mean near the front or near the back of the body respectively. Thus, for the knee joint described herein anterior refers to that portion of the knee that is nearer the front of the body when the leg is in an extended position. Proximal and distal mean nearer to or further from the root of the structure respectively. For example, the distal femur is a part of the knee joint while the proximal femur is closer to the hip joint. Finally, the adjectives medial and lateral mean nearer the median plane or further from the median plane respectively. The median plane is an imaginary, vertical plane through the middle of the body that divides the body into right and left halves.

Referring now to FIG. 1, a first embodiment of the present invention, unicondylar femoral component 100, comprises arcuated articular surface 110, bone contacting surface 120 disposed generally opposite articulating surface 110, post 130 extending superiorly from the posterior end of bone contacting surface 120, flange 140 extending superiorly from the anterior edge of femoral component 100, and porous layer 150 disposed against the entirety of bone contacting surface 120.

In a PKA, femoral component 100 is attached to one condyle of a "prepared" distal femur. ("Prepared" refers to a femur that has been cut appropriately to receive a condylar implant.) Although only one condyle is shown, it will be apparent to those skilled in the art, that the invention described and claimed herein is appropriately used for either femoral condyle.

As viewed from the distal portion to the superior portion of the implant, femoral component 100 comprises articulating surface 110. Articulating surface 110 comprises a generally arcuated shape between its anterior and posterior ends. The arcuated shape of articulating surface 110 is adapted to slidingly engage a unicondylar bearing component or a natural meniscus (neither of which is shown) disposed between femoral component 100 and a tibial component (also not shown).

Referring again to FIG. 1, femoral component 100 further comprises bone contacting surface 120 disposed generally superiorly and opposite to articulating surface 110. Bone contacting surface 120 preferably comprises a plurality of interconnected flat planes corresponding to bone cuts made to the distal femur. These bone cuts are made in order to prepare a compartment of the femur, i.e. one condyle, to receive femoral component 100.

Referring still to FIG. 1, femoral component 100 further comprises posterior post 130 extending generally superiorly from bone contacting surface 120. Post 130 may comprise any geometric shape including a rectangle or pyramid, but a generally cylindrical shape is preferred.

The anterior tip of femoral component 100 comprises flange 140. Flange 140 extends generally superiorly from femoral component 100 such that articular surface 110 extends anteriority and superiorly as shown in FIG. 1.

Anterior flange 140 and posterior post 130 are arranged such that an angle theta, as shown in FIG. 1 of about 1 degree to about 15 degrees is included between post 130 and flange 140. However, an angle of about 5 degrees is optimal. Included angle theta allows femoral component 100 to generate a clamping force on the distal femur thereby securing femoral component 100 to the distal femur via a press fit.

Continuing to refer to FIG. 1, porous surface 150 is disposed against bone contacting surface 120. Porous layer 150 generally comprises a depth of about 0.5 mm to about 5 mm. Porous layer 150 may comprise a beaded layer of commercially pure titanium, commercially pure cobalt alloys of the same, or a layer of structured porous tantalum such as Trabecular Metal™ a trademark of Implex corporation. Porous layer 150 provides a surface that promotes bony ingrowth of the distal femur into femoral component 150. This boney ingrowth provides for better fixation of femoral component 150 onto the distal femur. Such boney ingrowth also allows femoral component 100 to more accurately simulate a natural knee in terms of transferring load between femoral component 100 and the patient's femur.

Figure 2:
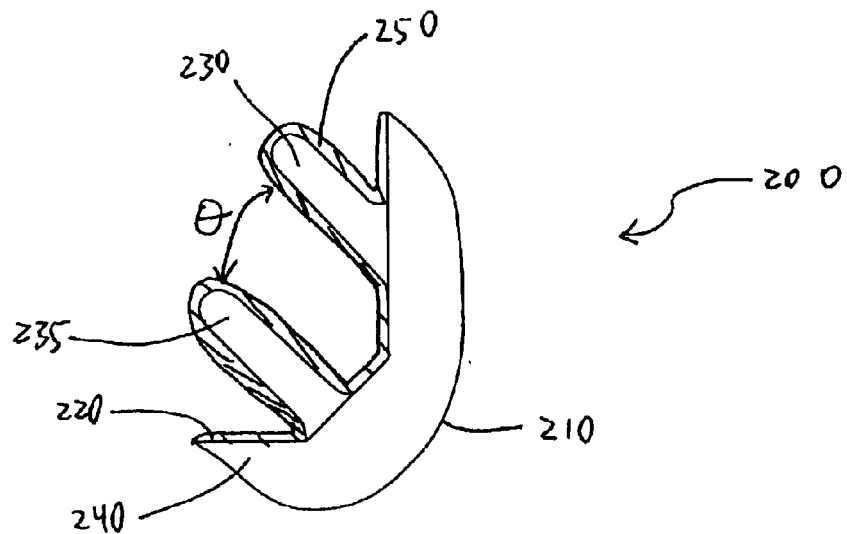
FIG. 2 is a side elevational view of a second embodiment of the present invention.

Referring now to FIG. 2, there showed a second embodiment of the present invention wherein femoral component 200 comprises arcuated articular surface 110, bone contacting surface 220 disposed generally opposite to articulating surface 210, posterior post 230 extending superiorly from bone contacting surface 220, anterior post 235 extending superiorly from bone contacting surface 220, flange 240 extending superiorly from the anterior edge of femoral component 200, and porous layer 250 disposed against the entirety of bone contacting surface 220.

Referring still to FIG. 2, there is shown femoral component 200 which generally comprises the same configuration as femoral component 100. However, femoral component 200 further comprises anterior post 235. Anterior post 235 and posterior post 230 are arranged along bone contacting surface 220 such that an angle of about 1 degree to about 15 degrees is disposed there between. In the embodiment shown in FIG. 2, the clamping force on the distal femur is generated between anterior post 235 and posterior post 230. It is preferred for the angle between these posts to be about 5 degrees.

Figure 3:
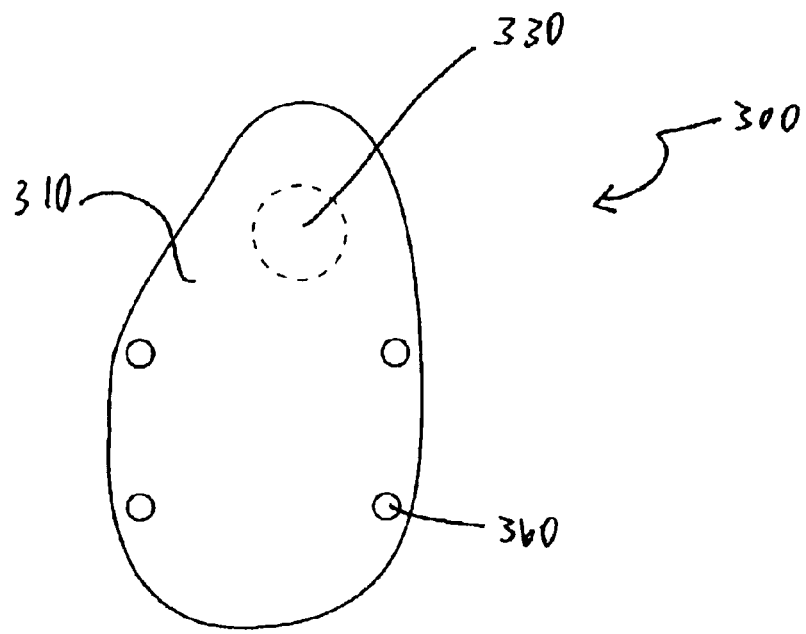
FIG. 3 is a bottom view of a third embodiment of the present invention.
Figure 4:
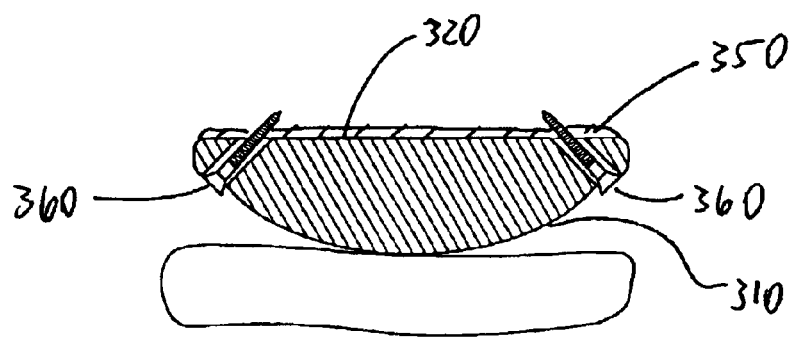
FIG. 4 is a side cross-sectional view of the third embodiment of the present invention.

Referring now to FIG. 3 to FIG. 4, there is shown a bottom view of unicondylar femoral component 300 according to a third embodiment of the present invention. Generally, the configuration of femoral component 300 is identical in a preferred embodiment to that of femoral component 100 or femoral component 200 except that femoral component 300 further comprises threaded fasteners 360. Femoral component 300 preferably comprises arcuated articular surface 310, bone contacting surface 320, post 330, bone contacting surface 320, flange 340, porous layer 350 disposed against bone contacting surface 320, and at least two threaded fasteners disposed in a desired arrangement through femoral component 300 and into a patient's distal femur such that threaded fasteners 360 fixedly attached femoral component 300 to the distal femur. Threaded fasteners 360 are arranged such that the heads of the threaded fasteners 360 do not interfere with the motion of articulating surface 310 relative to artificial or natural bearing surface 400 of a patient's knee. It is further preferred that femoral component 300 comprise four screws relatively symmetrically arranged through articulating surface 310 of femoral component 300. However, fewer threaded fasteners 360 may be employed while remaining within the scope of the appended claims. Moreover, while it is preferred to use one post extending superiorly from bone contacting surface 320, of femoral component 300, two or no posts may be used as well as porous layer 350 or no porous layer while still remaining within the scope of the appended claims.

It will be appreciated by those skilled in the art, that the foregoing is a description of preferred embodiments of the present invention and that variations in design and construction may be made to the preferred embodiments without departing from the scope of the invention as defined by the appended claims.

I claim:

1. The femoral component of a unicondylar endoprosthetic knee which lacks an anterior flange, wherein said femoral component is attached to the distal femur during a partial knee arthroplasty, the femoral component comprising:

a convex arcuated articulating surface having a desired shape suitable for unicondylar femoral component;

a bone contacting surface disposed opposite the articulating surface, wherein the contacting surface comprises a post extending from the bone contacting surface; and a flange disposed on an interior end of the femoral component, said post being inclined toward said flange such that an angle of about 5 degrees is formed between the flange and the post;

wherein interference between said flange, said post and the femur generates a clamping force securing the femoral component to the distal femur.

2. The femoral component of claim 1, wherein the component comprises a material selected from the group consisting of cobalt-chrome alloy, titanium alloy, commercially pure titanium, and commercially pure cobalt.

3. The femoral component of claim 1, further comprising a porous layer attached to the bone contacting surface.

4. The femoral component of claim 3, wherein the porous layer comprises structured porous tantalum.

5. The femoral component of claim 1 or 3 further comprising at least two threaded fasteners, the fasteners disposed through the femoral component into the distal femur such that the fasteners do not interfere with the motion of the femoral component against a bearing surface.

6. The femoral component of claim 1, wherein said flange and said post cooperatively define an angle of between about 1 degree and about 15 degrees.

* * * * *